United States Patent
Saijo

(10) Patent No.: US 9,151,702 B2
(45) Date of Patent: Oct. 6, 2015

(54) SAMPLE, SAMPLE FABRICATION APPARATUS, AND SAMPLE OBSERVATION METHOD

(71) Applicant: KABUSHIKI KAISHA TOSHIBA, Tokyo (JP)

(72) Inventor: Fumihiko Saijo, Yokkaichi (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 227 days.

(21) Appl. No.: 13/971,586

(22) Filed: Aug. 20, 2013

(65) Prior Publication Data

US 2014/0234529 A1    Aug. 21, 2014

(30) Foreign Application Priority Data

Feb. 18, 2013    (JP) .................................. 2013-029109

(51) Int. Cl.
 G01N 1/28    (2006.01)
(52) U.S. Cl.
 CPC ................ *G01N 1/2813* (2013.01); *G01N 1/28* (2013.01); *G01N 1/2806* (2013.01); *G01N 2223/611* (2013.01); *Y10T 428/13* (2015.01)
(58) Field of Classification Search
 CPC . G01N 1/28; G01N 1/2806; G01N 2223/611; Y10T 428/13
 See application file for complete search history.

(56) References Cited

U.S. PATENT DOCUMENTS

| 6,303,399 | B1 * | 10/2001 | Engelmann et al. | 438/14 |
| 6,388,265 | B1 * | 5/2002 | Chang et al. | 250/559.44 |
| 6,616,784 | B2 * | 9/2003 | Chang et al. | 156/154 |
| 6,849,298 | B2 * | 2/2005 | Pyo | 427/250 |
| 7,205,247 | B2 * | 4/2007 | Lee et al. | 438/785 |
| 7,560,692 | B2 * | 7/2009 | Barton et al. | 250/307 |
| 8,016,945 | B2 * | 9/2011 | Zilbauer et al. | 118/715 |
| 2006/0270223 | A1 * | 11/2006 | Millward | 438/681 |
| 2012/0126303 | A1 | 5/2012 | Arai et al. | |
| 2012/0241910 | A1 | 9/2012 | Ogi et al. | |

FOREIGN PATENT DOCUMENTS

| JP | 2002310941 A | 10/2002 |
| JP | 2003335740 A | 11/2003 |
| JP | 2005-308400 A | 11/2005 |
| JP | 2006-029974 A | 2/2006 |

OTHER PUBLICATIONS

Journal of Technical Disclosure No. 2012-501698, Japan Institute for Promoting Invention and Innovation, Apr. 4, 2012 (and English translation thereof).

Japanese Office Action (and English translation thereof) dated May 29, 2015, issued in counterpart Japanese Application No. 2013-029109.

* cited by examiner

*Primary Examiner* — Jack Berman

(74) *Attorney, Agent, or Firm* — Holtz, Holtz, Goodman & Chick PC

(57) ABSTRACT

In accordance with an embodiment, a sample includes a base material and a metal-based heavy element compound. The base material includes a tunnel structure portion with a cavity portion. The metal-based heavy element compound fills the cavity portion of the tunnel structure portion. The metal-based heavy element compound has a thickness that at least locally allows passage of a charged particle beam.

20 Claims, 8 Drawing Sheets

US 9,151,702 B2

SAMPLE, SAMPLE FABRICATION APPARATUS, AND SAMPLE OBSERVATION METHOD

CROSS REFERENCE TO RELATED APPLICATIONS

This application is based upon and claims the benefit of priority from the prior Japanese Patent Application No. 2013-029109, filed on Feb. 18, 2013, the entire contents of which are incorporated herein by reference.

FIELD

Embodiments described herein relate generally to a sample, a sample fabrication apparatus, and a sample observation method.

BACKGROUND

To observe a fine structure of a semiconductor device, a Transmission Electron Microscope (which will be referred to as a "TEM" hereinafter) that enables observation at the atomic level is used. A sample for such a TEM is fabricated by extracting a sample from a semiconductor device by using a Focused Ion Beam (which will be referred to as an "FIB" hereinafter) and processing it.

To secure and facilitate highly accurate observation using the TEM, fabricating a high-grade TEM sample that retains its original shape and is thin and robust is demanded.

BRIEF DESCRIPTION OF THE DRAWINGS

In the accompanying drawings.

DETAILED DESCRIPTION

In accordance with an embodiment, a sample includes a base material and a metal-based heavy element compound. The base material includes a tunnel structure portion with a cavity portion. The metal-based heavy element compound fills the cavity portion of the tunnel structure portion. The metal-based heavy element compound has a thickness that at least locally allows passage of a charged particle beam.

Embodiments will now be explained with reference to the accompanying drawings. Like components are provided with like reference signs throughout the drawings and repeated descriptions thereof are appropriately omitted.

It is to be noted that a description will be given as to a sample used for grasping a shape of an air gap in an NAND flash memory device, but the present invention is not restricted thereto as a matter of course, and it can be applied to samples in general each having a narrow tunnel structure.

(1) Sample

Figure 1:
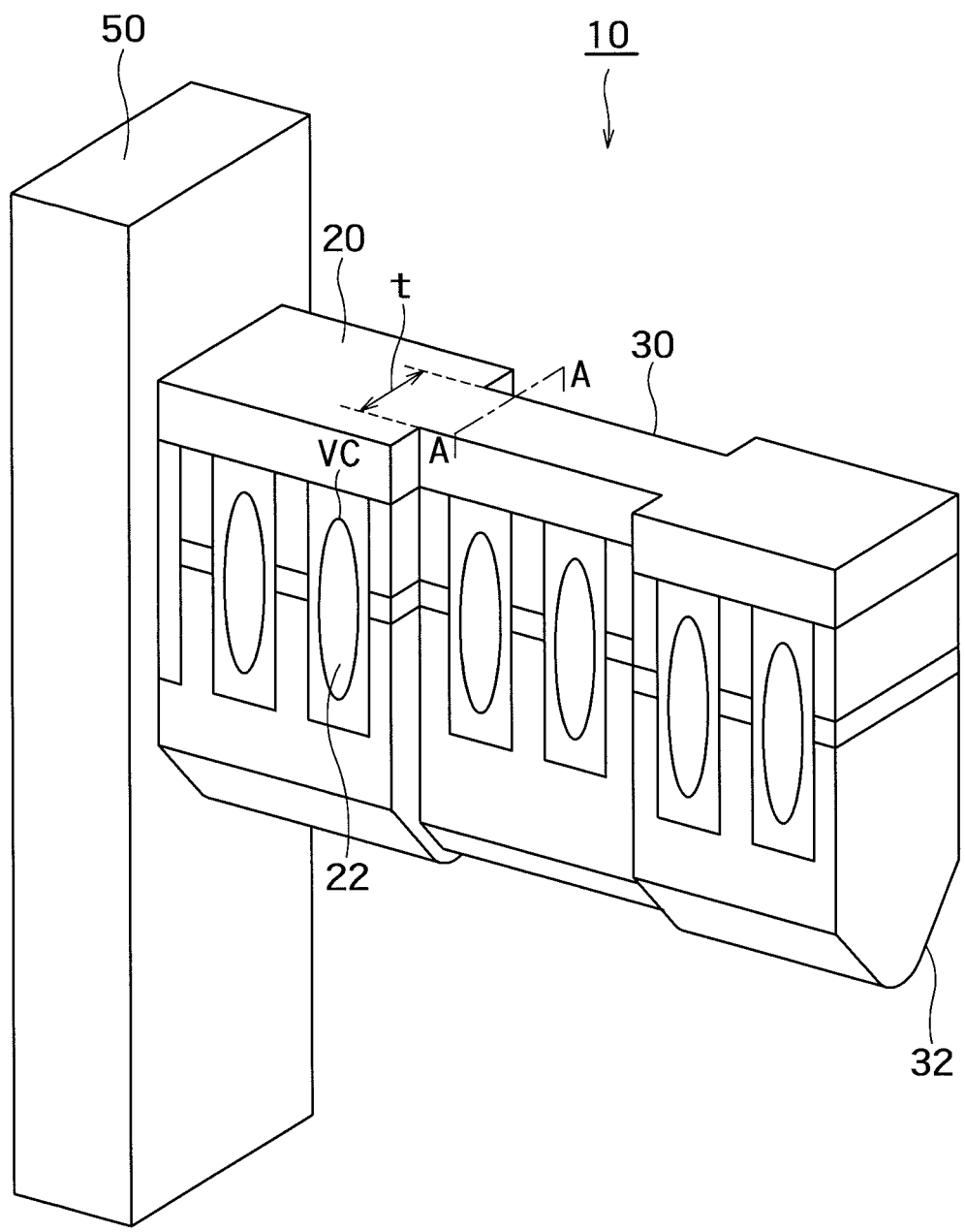
FIG. 1 is a perspective view of a sample according to a first embodiment.

FIG. 1 is a perspective view showing a sample according to a first embodiment. A sample 10 shown in FIG. 1 is fabricated by slicing out a wafer piece from an NAND flash memory device (not shown) and processing it, and one side surface of a base material 20 including a tunnel structure portion is fixed to a substrate 50 with use of an adhesive.

A cavity portion VC in the tunnel structure portion is filled with a metal-based heavy element compound 22. In this embodiment, as the metal-based heavy element compound 22, $Ta_2O_5$ can be also used besides $TiO_2$, for example.

Figure 2:
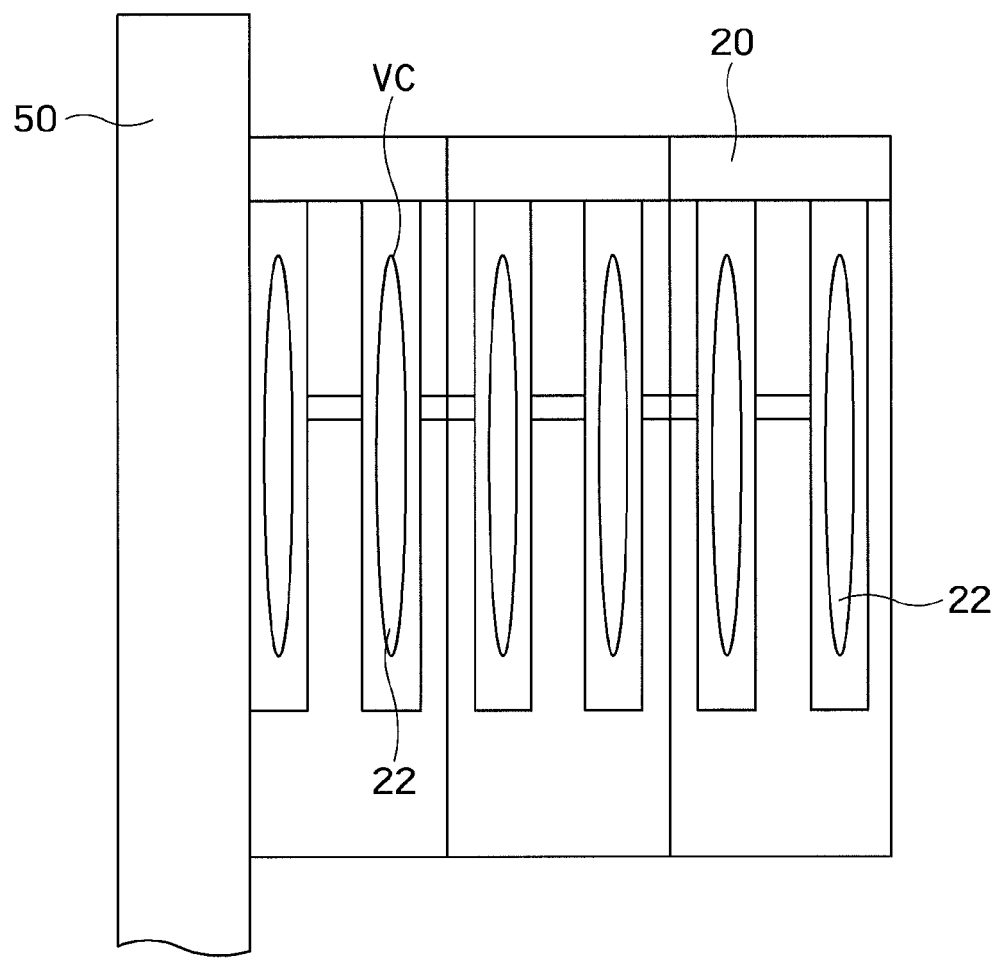
FIG. 2 is an enlarged front view of the sample shown in FIG. 1.

A concave portion 30 is formed at a front central portion of the sample 10, and a film thickness t of the metal-based heavy element compound 22 in this concave portion 30 is a thickness preferable for observation using a non-illustrated TEM, e.g., 10 nm to 20 nm. FIG. 2 is an enlarged view of a front side of the sample 10.

A U-shaped or V-shaped projection 32 is formed at an end portion of the sample 10 on a bottom surface side.

Figure 3:
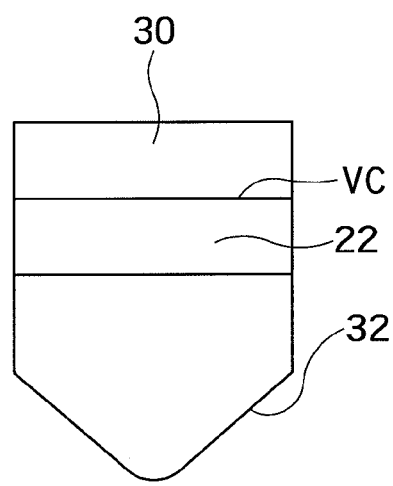
FIG. 3 is an end view taken along a cutting-plane line A-A shown in FIG. 1.
Figure 9:
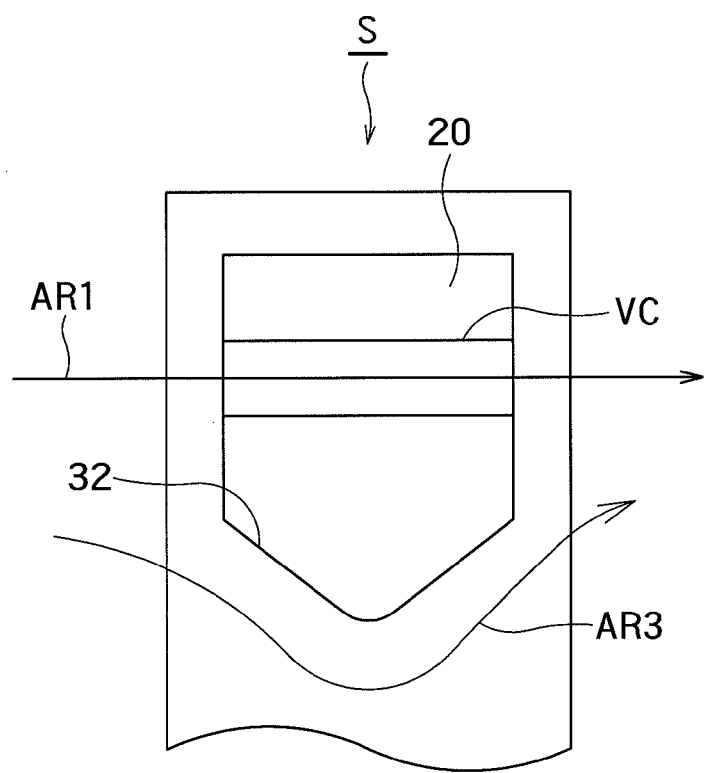
FIG. 9 is a view for explaining a relationship between a wafer piece and a gas current in a chamber of a sample fabrication apparatus depicted in FIG. 5.

FIG. 3 is an end view in a thickness direction of the concave portion 30 of the sample 10, i.e., a cutting-plane line A-A in FIG. 1. The projection 32 functions to promote a smooth flow of a reactant gas in a process of filling the cavity portion VC with the metal-based heavy element compound 22 (see an arrow AR3 in FIG. 9).

This point will be described later in detail in conjunction with a subsequent embodiment of a sample fabrication apparatus.

In the embodiment shown in FIG. 1, the conformation that the cavity portion VC is filled with the single metal-based heavy element compound 22, but filling this cavity portion VC is not restricted to this conformation, and a plurality of compounds may be laminated and fill the cavity portion VC.

Figure 4:
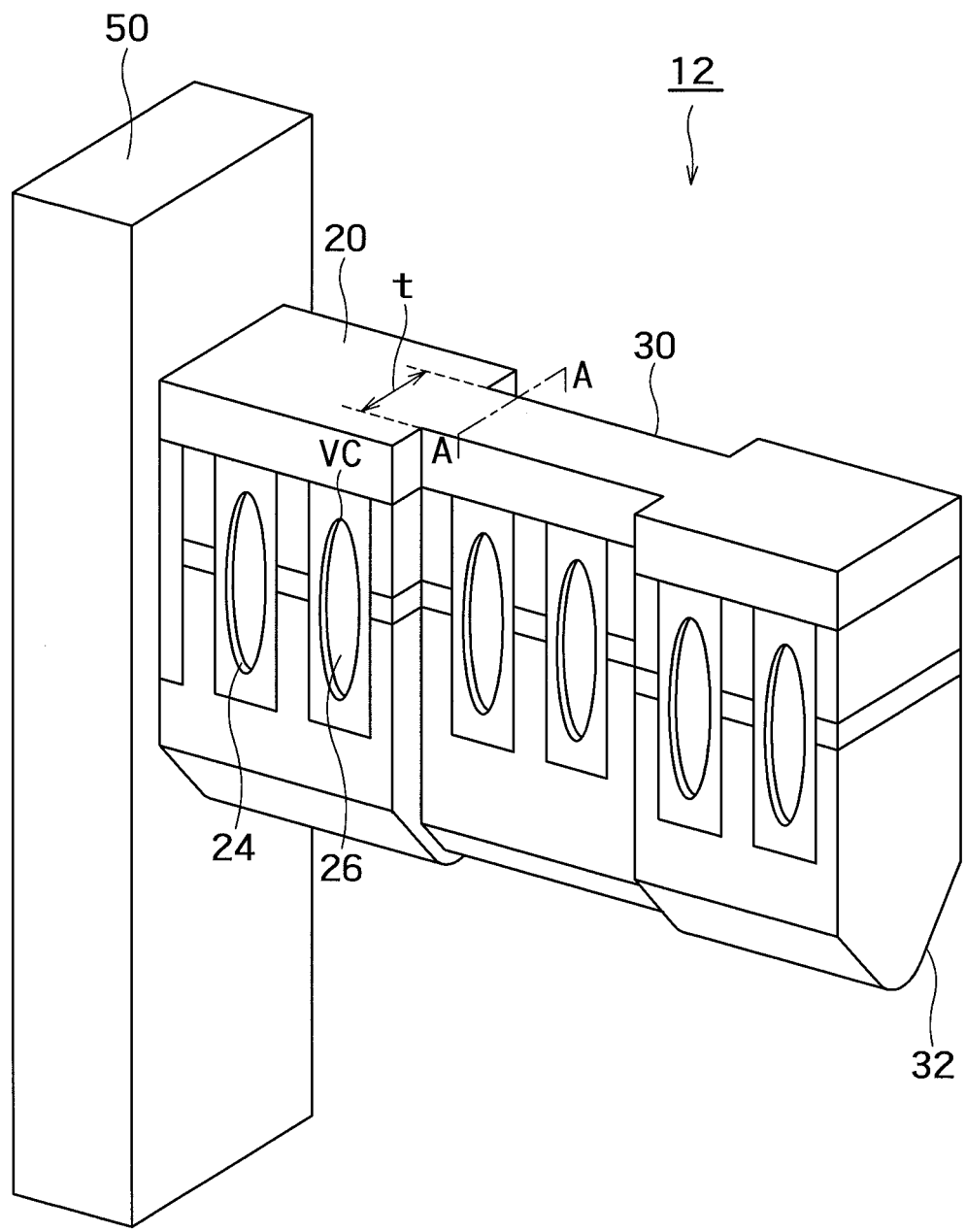
FIG. 4 is a perspective view of a sample according to a second embodiment.

FIG. 4 is a perspective view of a sample according to a second embodiment. In this embodiment, a cavity portion VC is filled with two types of compounds.

In a sample 12 shown in FIG. 4, on an edge part, i.e., an inner peripheral surface part of the cavity portion VC, a thin film 24 that can obtain a contrast difference relative to a base material 20 in a TEM observation image is formed. Therefore, a shape of the edge of the cavity portion VC can be observed with a high accuracy. As the thin film 24, there are, e.g., a hafnium oxide ($HfO_2$) as well as a tantalum oxide ($Ta_2O_5$), a zirconium oxide ($ZrO_2$), and others.

Further, the cavity portion VC is filled with a metal-based heavy element compound 26 to fill the cavity portion VC via the thin film 24. As a material of the metal-based heavy element compound 26, a material having the same processibility as the processibility of the base material is selected, e.g., an aluminum oxide ($Al_2O_3$) can be taken as an example. Other structures of the sample 12 are substantially the same as those of the sample 10 shown in FIG. 10.

According to the sample of at least one of the foregoing embodiments, since the cavity portion of the tunnel structure portion is filled with the metal-based heavy element compound, thus a possibility of deformation due to stress and the like is low, and their thinness and robustness facilitate handling, thereby highly accurate observation using the TEM can be assuredly performed.

(2) Sample Fabrication Apparatus and Fabrication of Sample

Figure 5:
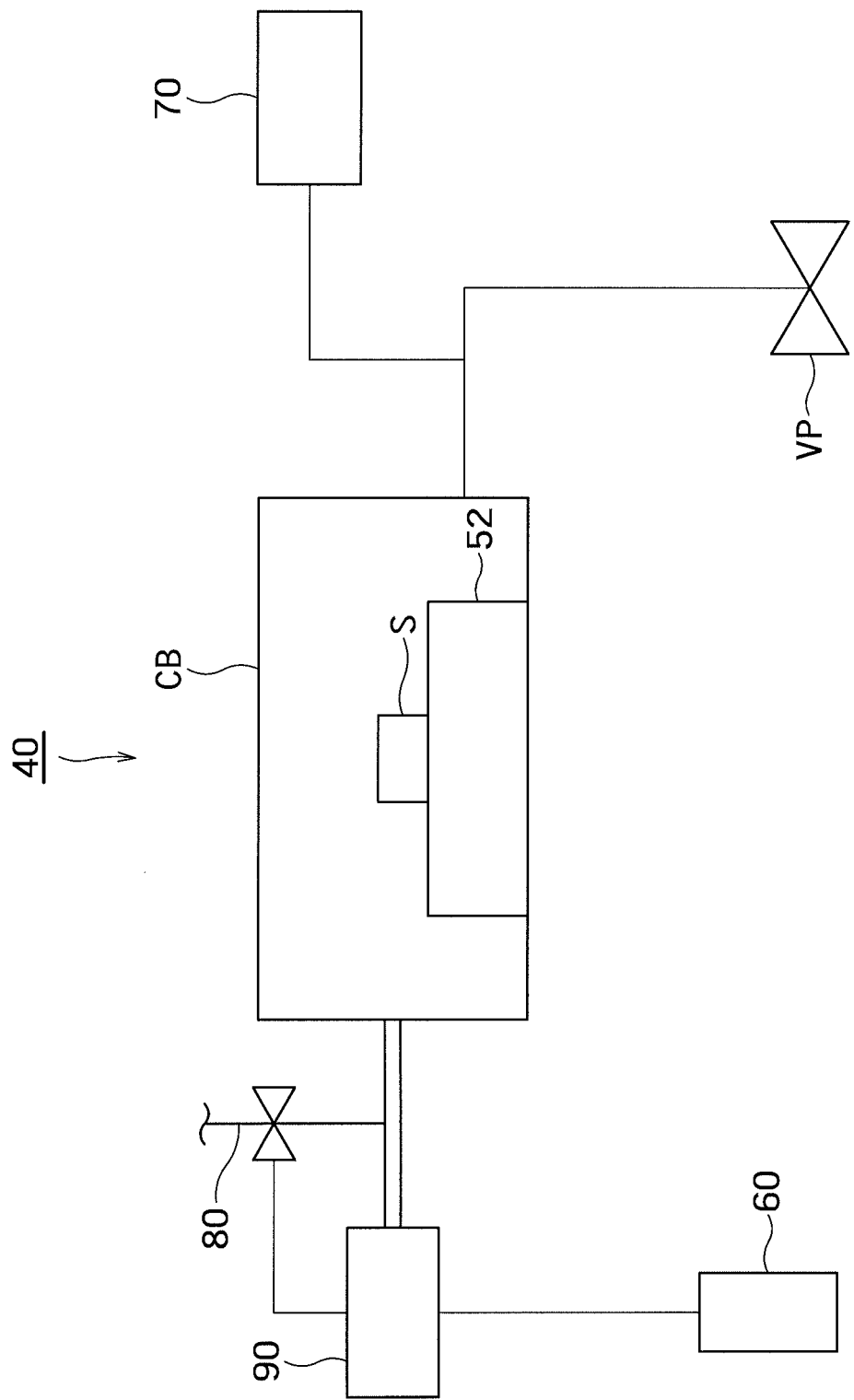
FIG. 5 is a block diagram showing an outline configuration of a sample fabrication apparatus according to a first embodiment.

FIG. 5 is a block diagram showing an outline configuration of a sample fabrication apparatus according to a first embodiment. The sample fabrication apparatus 40 shown in FIG. 5 includes a chamber CB, a gas source 60, a gas recovery unit 70, a vacuum pump VP, an oxidant addition pipe 80, and a gas flow rate control unit 90.

The chamber CB includes a stage 52 configured to hold a wafer piece S which is sliced out from a wafer with a semiconductor device formed thereon and has a narrow tunnel structure. The vacuum pump VP exhausts the chamber CB of air to form a vacuum state.

The gas source 60 stores a gas containing a metal-based heavy element and supplies a reactant gas to the chamber CB through the gas flow rate control unit 90. In this embodiment, as the reactant gas, Tetrakis Dimethyl Amido Hafnium (TDMAHf) is used in a case where the cavity portion of the tunnel structure portion is filled with a hafnium oxide ($HfO_2$), and Pentakis Dimethyl Amido Tantalum (PDMATa) is used in a case where the cavity portion is filled with a tantalum oxide ($Ta_2O_5$).

An oxidant is added to the gas in the oxidant addition pipe 80 under control of the gas flow rate control unit 90. In this embodiment, the oxidant is water ($H_2O$).

The gas flow rate control unit 90 controls a gas flow rate from the gas source 60 in accordance with a processed state of the wafer piece S. The gas flow rate control unit 90 also controls the oxidant addition pipe 80 so that the oxidant can be added according to a gas flow rate.

The gas recovery unit 70 recovers the gas discharged from the chamber CB.

A sample fabrication method using the sample fabrication apparatus 40 depicted in FIG. 5 will now be described with reference to FIG. 6 to FIG. 9.

Figure 6:
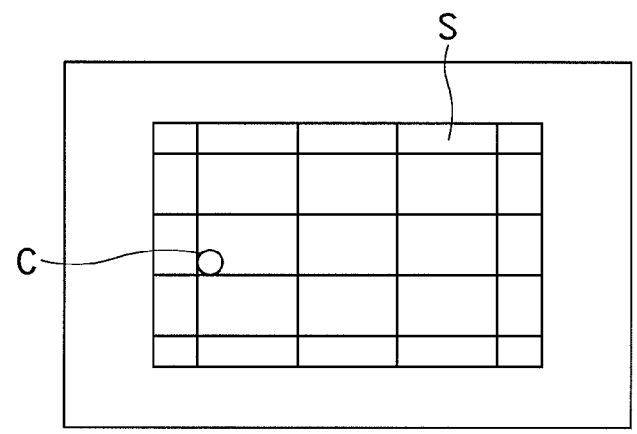
FIG. 6 is a view showing an example of a wafer piece.
Figure 7:
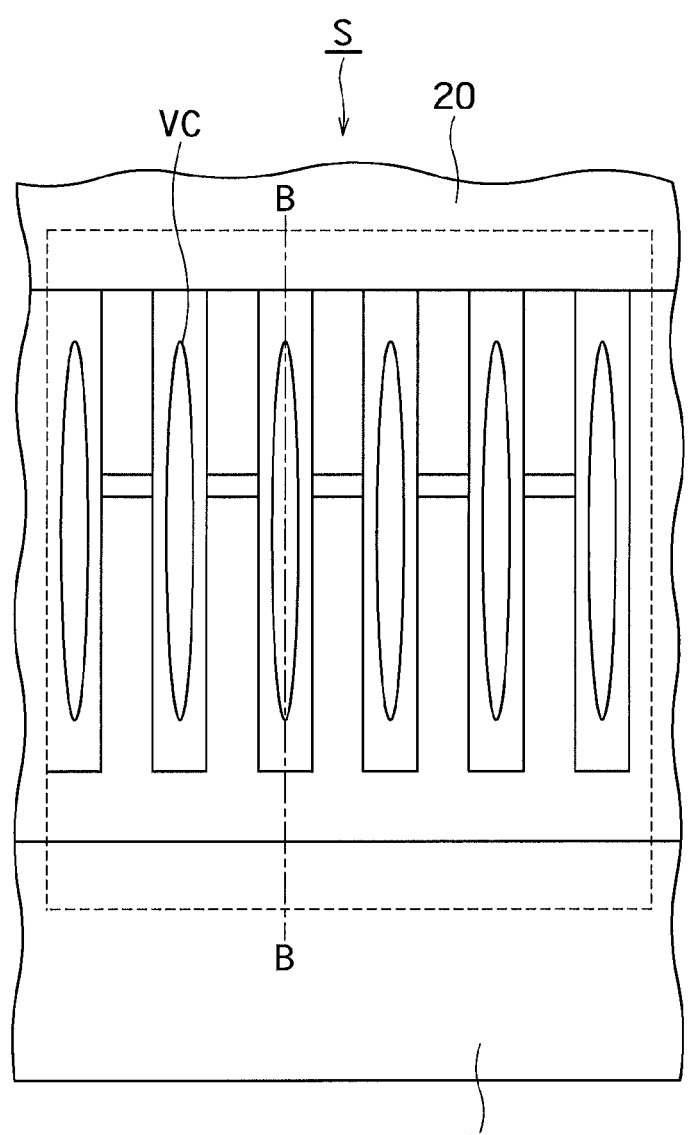
FIG. 7 is a partially enlarged view of FIG. 6.

First, a wafer piece is sliced out of a wafer with a semiconductor device formed thereon as an examination target as preprocessing. In this embodiment, an NAND flash memory device (not shown) is used as the semiconductor device. The wafer piece S including an air gap portion as the tunnel structure portion is sliced out of the device wafer by using an FIB. FIG. 6 shows an example of the wafer piece S. FIG. 7 is an enlarged view of a portion represented by a circle C in FIG. 6, and FIG. 8 is a cross-sectional view taken along a cutting-plane line B-B in FIG. 7.

Figure 8:
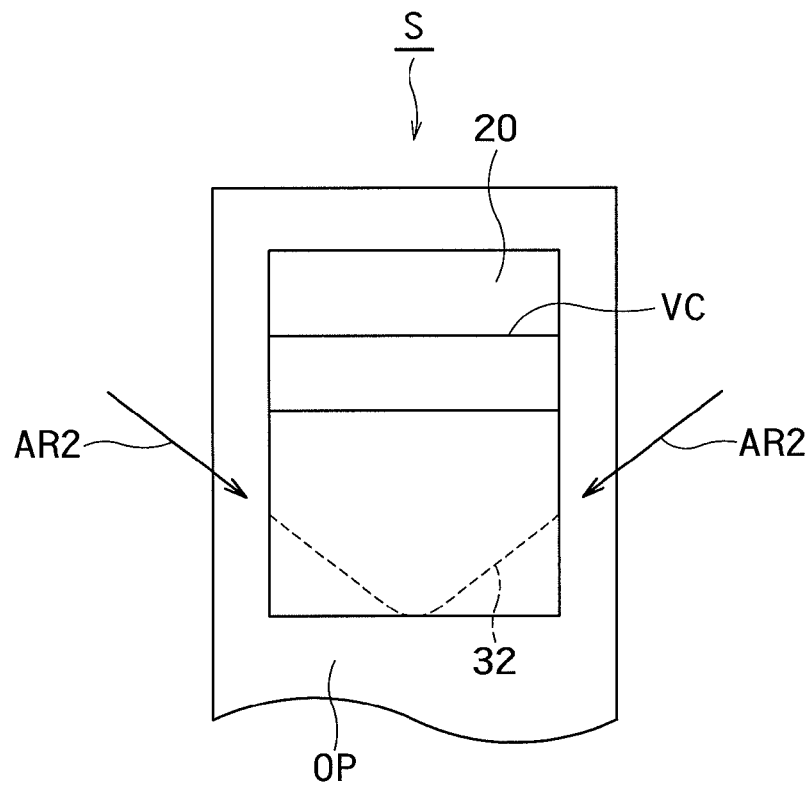
FIG. 8 is a cross-sectional view taken along a cutting-plane line B-B in FIG. 7.

Then, as represented by a reference sign OP in FIG. 7 and FIG. 8, a portion of the wafer piece S region that is apart from the cavity portion VC by a predetermined length is irradiated with the FIB, thereby forming an opening OP.

At this time, slicing is carried out so that a projection 32 in a U-like or V-like shape can be formed in a cut plane along the direction A-A in FIG. 1 when the FIB is also applied in a direction 35 represented by an arrow AR3 in FIG. 8.

Then, the fabrication advances to a process of ALD (Atomic Layer Deposition) using the sample fabrication apparatus 40 in FIG. 5.

First, the wafer piece S is disposed on the stage 52 and held by the stage 52 in the chamber CB. At this time, as indicated by an arrow AR1 in FIG. 9, the wafer piece S is disposed in such a manner that a direction running through the cavity portion VC of the tunnel structure portion substantially coincides with a gas inflow direction.

Subsequently, the reactant gas is introduced into the chamber CB from the gas source 60 while controlling a gas flow rate by the gas flow rate control unit 90. At this time, as indicated by an arrow AR3 in FIG. 9, since the wafer piece S has the projection 32 on its bottom portion, the gas current flows through the opening OP without becoming turbulent, smoothly passes through the cavity portion VC, and is then recovered by the recovery unit 90.

Such a gas current realizes formation of a titanium oxide ($TiO_2$) in the cavity portion VC, and the cavity portion VC is thereby filled. Subsequently, the wafer piece S is taken out of the chamber CB, a small base material in a desired size (e.g., a region indicated by a dotted line in FIG. 7) is extracted from the wafer piece S by the FIB, a side surface of this material is fixed to the substrate 50 (see FIG. 1) by an adhesive, and the concave portion 30 is formed in a central part of its front surface, thereby fabricating the sample 10 which is shown in FIG. 1.

For comparison, as a reference example, a method of dripping a high-polymer material, e.g., a resin into the cavity portion to form a buried layer will now be taken up. According to this method, although the burying process itself is simple, the buried layer does not stay in the cavity portion, and protruding portions are formed on both a front side and a back side of the sample S. Therefore, the protruding portions on both the front side and the back side of the sample S must be again ground down until these sides become level with the side surface of the base material. During this re-grinding process, a resin surface may be damaged or a blind-like pattern may be formed on this surface by shavings, which can be a cause that deteriorates the accuracy in the subsequent TEM observation. Moreover, a shape/size of the cavity portion VC is not necessarily uniform, and hence unevenness may be produced in both the burying process and the re-grinding process.

Figure 10:
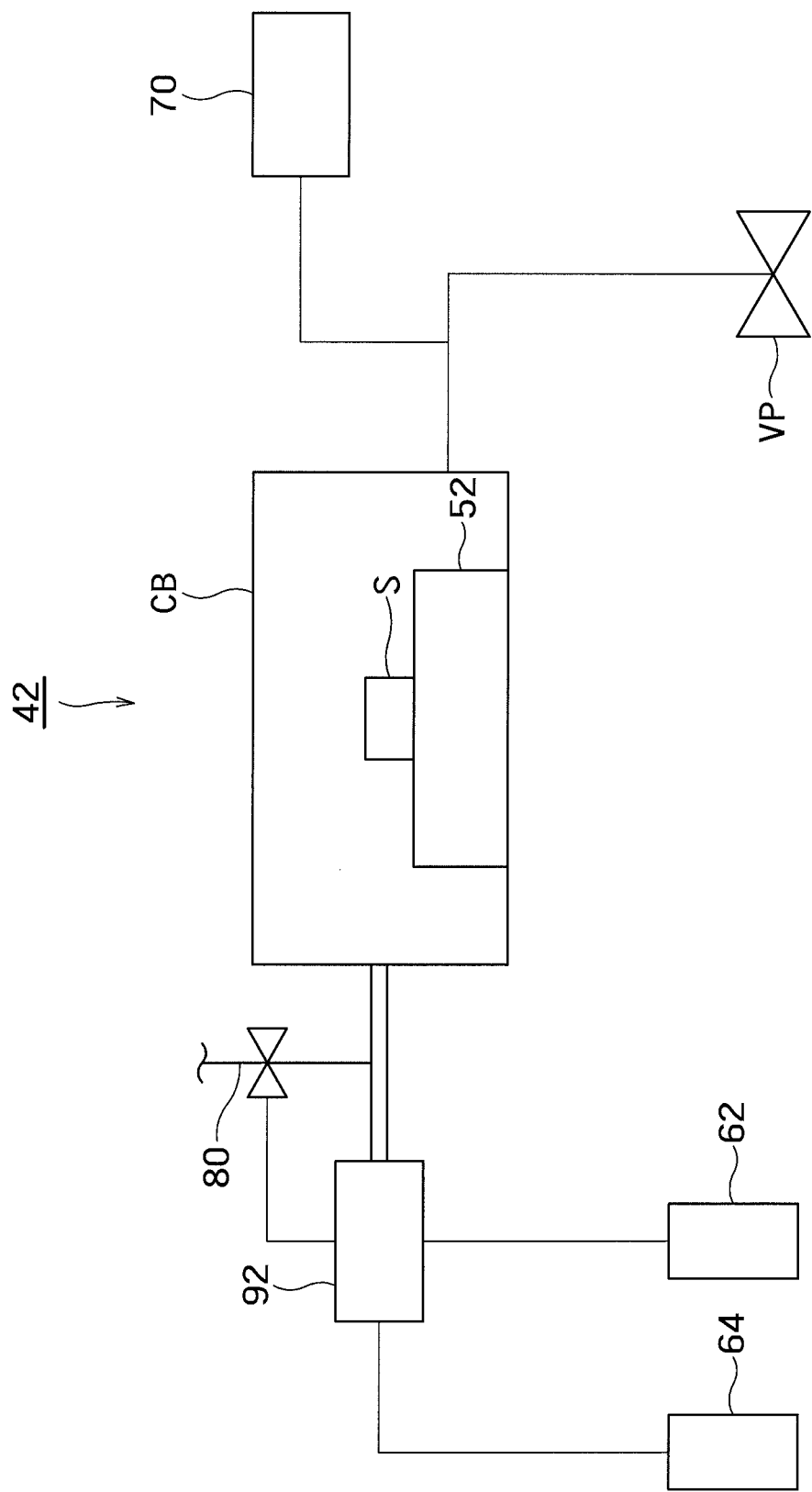
FIG. 10 is a block diagram showing an outline configuration of a sample fabrication apparatus according to a second embodiment.

FIG. 10 is a block diagram showing an outline configuration of a sample fabrication apparatus according to a second embodiment. As obvious from comparison with the sample fabrication apparatus 40 depicted in FIG. 5, a sample fabrication apparatus 42 according to this embodiment includes a first gas source 62 and a second gas source 64 and also includes a gas flow rate control unit 92 that controls both gas flow rates from these gas sources 62 and 64. Other structures of the sample fabrication apparatus 42 are substantially the same as those in the sample fabrication apparatus 40 depicted in FIG. 5.

In this embodiment, a gas containing Tetrakis Dimethyl Amido Hafnium (TDMAHf) is used as the first gas source, and a gas containing TMA (trimethylaluminum) is used as the second gas source. The sample fabrication method using the sample fabrication apparatus 42 shown in FIG. 10 is as follows.

First, as described above, the wafer piece S is sliced out of a wafer with a semiconductor device formed thereon as an examination target, a portion of the wafer piece S region that is apart from the cavity portion VC by a predetermined length is irradiated with the FIB, thereby forming an opening OP (see FIG. 7 and FIG. 8). At this time, slicing is carried out so that the projection 32 in a U-like or V-like shape can be formed in a cut plane along the direction A-A in FIG. 1 when the FIB is also applied in a direction represented by an arrow AR2 in FIG. 8.

Then, the wafer piece S is held by a stage 52 of the sample fabrication apparatus 42 shown in FIG. 10 in such a manner that a direction running through the cavity portion VC (see FIG. 9) of the tunnel structure portion coincides with a gas inflow direction.

Then, the reactant gas is introduced into the chamber CB from the first gas source 62 while controlling a gas flow rate by the gas flow rate control unit 92, and a thin film 24 made of a hafnium oxide ($HfO_2$) is formed at an edge part, i.e., an inner peripheral surface part of the cavity portion VC (see FIG. 4).

Subsequently, the gas source is switched from the first gas source 62 to the second gas source 64, the reactant gas is introduced into the chamber CB from the second gas source 64 while controlling a gas flow rate by the gas flow rate control unit 92, and the cavity portion VC is filled with a compound 26 which is made of an aluminum oxide ($Al_2O_3$) and has the same processability as the processability of the base material to fill the cavity portion VC via the thin film 24 (see FIG. 4). Thereafter, the wafer piece S is taken out of the chamber CB, the small base material in a desired size is extracted from the wafer piece S by the FIB, a side surface of this material is fixed to the substrate 50 (see FIG. 4) by an adhesive, and a concave portion 30 is formed in a central part of its front surface, thereby fabricating the sample 12 which is shown in FIG. 4.

As described above, according to the second embodiment, the sample 12 that enables obtaining a contrast difference relative to the base material 20 in a TEM observation image can be fabricated.

Additionally, according to the sample fabrication apparatus based on at least one of the foregoing embodiments, since the reactant gas is used, a re-grinding process is no longer necessary. Furthermore, since the ALD method is used, a film formation temperature can be suppressed to a low value as compared with general metal thin film formation such as CVD (Chemical Vapor Deposition) or sputtering, and hence the base material cannot be damaged due to a surface reaction of the reactant gas, thereby fabricating the sample with high coverage and film thickness controllability.

(3) TEM Observation

Figure 11:
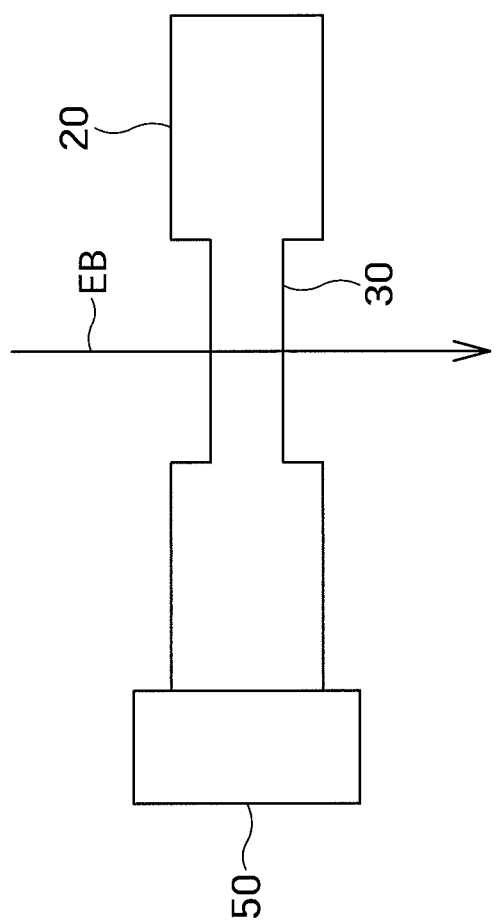
FIG. 11 is an explanatory view of an observation method of a sample according to an embodiment.

When a sample fabricated by using at least one of the above-mentioned sample fabrication apparatuses is disposed to a TEM apparatus (not shown) and an electronic beam EB is applied to acquire an observation image through a concave portion 30 as shown in FIG. 11, a shape of the cavity portion VC of a tunnel structure portion can be highly accurately observed. In this embodiment, the electronic beam EB corresponds to an electromagnetic radiation.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A sample comprising:
   a base material comprising a tunnel structure portion comprising a cavity portion; and
   a metal-based heavy element compound which fills the cavity portion of the tunnel structure portion,
   wherein the metal-based heavy element compound has a thickness that at least locally allows passage of a charged particle beam.

2. The sample of claim 1,
   wherein the metal-based heavy element compound comprises a first metal-based heavy element compound formed on an edge portion of the cavity, and a second metal-based heavy element compound that fills the cavity portion through the first metal-based heavy element compound.

3. The sample of claim 1, wherein a projection having a V-like or U-like shape in a cutting plane is provided at an end portion of the base material, the cutting plane being represented as a plane comprising a direction running through the cavity.

4. The sample of claim 1,
   wherein the metal-based heavy element compound is a titanium oxide ($TiO_2$).

5. The sample of claim 2,
   wherein the first metal-based heavy element compound is a hafnium oxide ($HfO_2$), a tantalum oxide ($Ta_2O_5$), or a zirconium oxide ($ZrO_2$), and
   the second metal-based heavy element compound is an aluminum oxide ($Al_2O_3$).

6. A sample fabrication apparatus comprising:
   a chamber which accommodates a wafer piece comprising a base material comprising a tunnel structure portion;
   a gas source which supplies a gas comprising a metal-based heavy element to the chamber through a cavity of the tunnel structure portion;
   a gas recovery unit which recovers the gas that has passed through the cavity; and
   a gas flow rate control unit which controls a flow rate of the gas.

7. The sample fabrication apparatus of claim 6,
   wherein the gas comprises Tetrakis Dimethyl Amido Titanium (TDMATi).

8. The sample fabrication apparatus of claim 6,
   wherein the gas comprises a first gas comprising a first metal-based heavy element, and a second gas comprising a second metal-based heavy element,
   the gas source comprises first and second gas sources which supply to the chamber the first and second gases which are used for forming first and second metal-based heavy element compounds, respectively, and
   the gas flow rate control unit allows the first gas to pass until the first metal-based heavy element compound is formed at an edge portion of the cavity, and allows the second gas to pass after the first metal-based heavy element compound is formed.

9. The sample fabrication apparatus of claim 8, wherein the first metal-based heavy element compound is a material that enables obtaining a contrast difference relative to the base material in an image acquired by irradiation of a charged particle beam.

10. The sample fabrication apparatus of claim 9,
    wherein the first metal-based heavy element compound is a hafnium oxide ($HfO_2$), a tantalum oxide ($Ta_2O_5$), or a zirconium oxide ($ZrO_2$).

11. The sample fabrication apparatus of claim 9,
    wherein the first metal-based heavy element compound is a hafnium oxide ($HfO_2$), and
    the first gas comprises a Tetrakis Dimethyl Amido Hafnium (TDMAHf).

12. The sample fabrication apparatus of claim 8,
    wherein the second metal-based heavy element compound comprises the same processability as that of the base material.

13. The sample fabrication apparatus of claim 11,
    wherein the second-metal based heavy element compound is an aluminum oxide ($Al_2O_3$), and
    the second gas comprises TMA (trimethylaluminum).

14. A sample observation method comprising:
fabricating a sample which comprises a base material comprising a tunnel structure portion, and a metal-based heavy element compound which fills a cavity of the tunnel structure portion and has a thickness which at least locally allows passage of a charged particle beam; and applying a charged particle beam to the sample and performing observation through the metal-based heavy element compound.

15. The sample observation method of claim 14, wherein fabricating the sample comprises:
allowing a gas comprising a metal-based heavy element to flow through the cavity of a wafer piece comprising the base material that comprises the tunnel structure portion and filling the cavity with a compound of the metal-based heavy element; and
extracting part of the base material filling the gap from the wafer piece and fixing the extracted part to a substrate.

16. The sample observation method of claim 15, wherein fabricating the sample further comprises providing an opening in the wafer piece before allowing the gas to flow in such a manner that a V-shaped or U-shaped projection is formed in a cutting plane in a thickness direction at an end portion of the extracted base material.

17. The sample observation method of claim 15, wherein the gas comprises Tetrakis Dimethyl Amido Titanium (TDMATi).

18. The sample observation method of claim 15, wherein the gas comprises a first gas comprising a first metal-based heavy element, and a second gas comprising a second metal-based heavy element with the same processibility as that of the base material in the sample, and
filling the cavity comprises allowing the first gas to flow until a compound of the first metal-based heavy element is formed on an edge portion of the cavity, and allowing the second gas to flow after the compound of the first metal-based heavy element is formed.

19. The sample observation method of claim 18, wherein the first metal-based heavy element compound is a material which enables obtaining a contrast difference relative to the base material of the sample in an image acquired by irradiation of the charged particle beam.

20. The sample observation method of claim 17, wherein the first metal-based heavy element compound is a hafnium oxide ($HfO_2$),
the first gas comprises Tetrakis Dimethyl Amido Hafnium (TDMAHf), and
the second gas comprises TMA (trimethylaluminum) and forms an aluminum oxide ($Al_2O_3$), and the cavity is filled through the hafnium oxide ($HfO_2$).

* * * * *